United States Patent [19]

Palladino et al.

[11] Patent Number: 5,189,019
[45] Date of Patent: Feb. 23, 1993

[54] ANTISTASIN DERIVED ANTICOAGULANT PROTEIN

[75] Inventors: Linda O. Palladino, Edison; Melvin Silberklang, Engelwood; Jwu-Sheng Tung, Cranbury; Simon W. Law, Westfield; George E. Mark, Princeton Junction, all of N.J.

[73] Assignee: Merck & Co., Inc., Rahway, N.J.

[21] Appl. No.: 512,695

[22] Filed: Apr. 23, 1990

[51] Int. Cl.⁵ .................. A61K 37/64; C07K 7/10
[52] U.S. Cl. ........................ 514/12; 530/324; 530/855; 930/250; 514/822
[58] Field of Search .......... 530/324, 350; 514/12; 435/212, 69.6

[56] References Cited

U.S. PATENT DOCUMENTS 4,752,603  6/1988  Collen et al. .................. 514/21
4,832,849  5/1989  Cardin .......................... 210/635

OTHER PUBLICATIONS

J. of Biological Chemistry "The Amino Acid Sequence of Antistasin" vol. 263 (21): 10162–10167, Jul. 25, 1988.

Primary Examiner—Garnette D. Draper
Assistant Examiner—Nina Ossanna
Attorney, Agent, or Firm—Richard S. Parr; Charles M. Caruso

[57] ABSTRACT

A protein having a molecular weight of about 6,000 daltons which is biologically active in the inhibition of Factor Xa during the blood coagulation cascade, a method for producing the protein, methods for inhibiting blood coagulation using the protein, and suitable pharmaceutical compositions.

3 Claims, 7 Drawing Sheets

ANTISTASIN VARIANT 2 cDNA CLONE FROM gt22 LIBRARY–FLANKED BY NotI AND Sal I
DIGESTED WITH NotI/Sal I
SUBCLONED INTO pUC18 (BRL) AT Sal I/NotI SITES
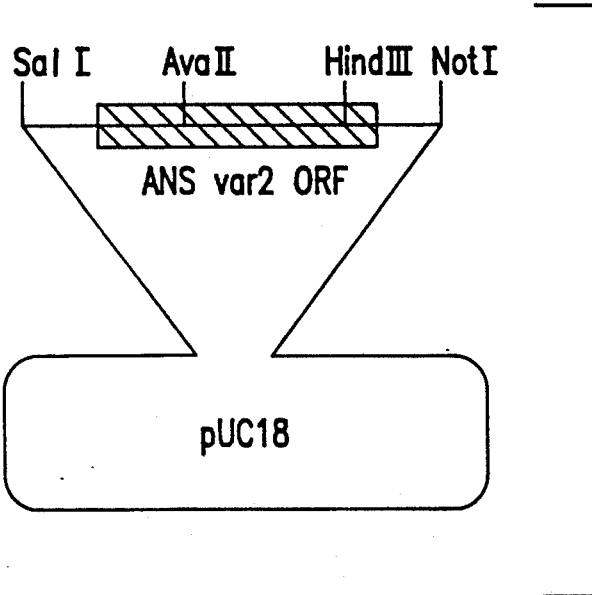
= K538
DIGESTED WITH
AvaII/HindIII
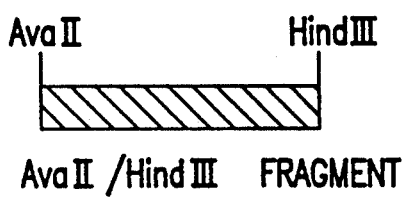
FIG.2

```
                                                                    +1
CCACC ATG ATT AAG TTG GCT ATT TTA TTG CTG TTC ACT GTT GCC ATA GTC CGT TGT CAA GGA
      Met Ile Lys Leu Ala Ile Leu Leu Leu Phe Thr Val Ala Ile Val Arg Cys Gln Gly
                                     10                              20

CCA TTT GGA CCC GGG TGT GAA GAG GCA GGA TGT CCA GAA GGT TCC GCG TGC AAC ATT ATT
Pro Phe Gly Pro Gly Cys Glu Glu Ala Gly Cys Pro Glu Gly Ser Ala Cys Asn Ile Ile
                                     30                              40

ACA GAC AGA TGC ACT TGT TCT GAG GTC AGA TGT CGT GTG CAC TGT CCG CAT GGA TTT CAG
Thr Asp Arg Cys Thr Cys Ser Glu Val Arg Cys Arg Val His Cys Pro His Gly Phe Gln

AGG AGC AGA TAC GGG TGT GAA TTC TGC AAA TGC AGA TTG GAG CCA ATG TAA
Arg Ser Arg Tyr Gly Cys Glu Phe Cys Lys Cys Arg Leu Glu Pro Met
                                     50
```

FIG. 3

```
                                                              -5
                                          -1  Met Ile Lys Leu Ala
                                              ATG ATT AAG TTG GCT
                                                             10
                    ↓1           Gly Pro Phe Gly Pro Gly Cys Glu Glu Ala
          -15                  5
Ile Leu Leu Phe Thr Val Ala Ile Val Arg Cys Gl                                                    
ATT TTA TTG CTG TTC ACT GTT GCC ATA GTC CGT TGT CAA GGA CCA TTT GGA CCC GGG TGT GAA GAG GCA
                                                                  30
                       15                 20                  25
Gly Cys Pro Glu Gly Ser Ala Cys Asn Ile Ile Thr Asp Arg Cys Thr Cys Ser Glu Val Arg Cys Arg
GGA TGT CCA GAA GGT TCC GCG TGC AAC ATT ATT ACA GAC AGA TGC ACT TGT TCT GAG GTC AGA TGT CGT
                                                                           Ile  55
                  35                         45                   50
Val His Cys Pro His Gly Phe Gln Arg Ser Arg Tyr Gly Cys Phe Cys Lys Cys Glu Leu Glu Pro
GTG CAC TGT CCG CAT GGA TTT CAG AGG AGC AGA TAC GGG TGT TTC TGC AAA TGC GAG TTG GAG CCA
```

FIG. 6

```
         60              65                  70              75                  80
Met Lys Ala Thr Cys Asp Ile Ser Glu Cys Pro Glu Gly Met Met Cys Ser Arg Leu Thr Asn Lys Cys
::: ::: ::: ::: ::: ::: ::: ::: ::: ::: ::: ::: ::: ::: ::: ::: ::: ::: ::: ::: ::: ::: :::
ATG AAA GCT ACA TGT GAC ATA AGC GAA TGC CCA GAA GGT ATG ATG TGT AGC AGA CTG ACC AAT AAG TGT
                     85                  90                  95                 100
Asp Cys Lys Ile Asp Ile Asn Cys Arg Lys Thr Cys Pro Asn Gly Leu Lys Arg Asp Lys Leu Gly Cys
::: ::: ::: ::: ::: ::: ::: ::: ::: ::: ::: ::: ::: ::: ::: ::: ::: ::: ::: ::: ::: ::: :::
GAT TGC AAG ATA GAC ATA GAC ATC AAC TGC AGA AAA ACC TGT CCA AAC GGC CTC AAA CGT GAT AAA CTT GGA TGC
                    105                 110                 115
Glu Tyr Cys Arg Pro Lys Arg Lys Leu Ile Pro Arg Leu Ser
::: ::: ::: ::: ::: ::: ::: ::: ::: ::: ::: ::: ::: :::
GAA TAT TGT AGG CCC AAG AGG AAG CTT ATC CCA CGC TTA TCA

FIG. 6 (Cont)
```

ANTISTASIN DERIVED ANTICOAGULANT PROTEIN

BACKGROUND OF THE INVENTION

Antistasin, a 15 kDa cysteine rich (20 cysteines of 119 amino acids) protein found in the salivary gland of the Mexican leech, *Haementeria officinalis*, has been shown to be a potent inhibitor of Factor Xa in the human blood coagulation cascade, Tuszynski et al., *J. Biol. Chem.* 262: 9718–9723 (1987); Nutt et al., *J. Biol. Chem.* 263: 10162–10167 (1988). Antistasin's ability to inhibit Factor Xa's activity, which can be activated by both the intrinsic and extrinsic pathways, makes it an attractive candidate for anticoagulant therapy. Furthermore, because antistasin inhibits the coagulation cascade at a step earlier than those anticoagulants acting on thrombin, such as hirudin and heparin, it has the potential of being a more efficient anticoagulant.

Sequence analyses show that antistasin possesses an internal homology between roughly the N-terminal and the C-terminal halves (40% for amino acids and 50% for nucleotides), Nutt et al., *J. Biol. Chem.* 263: 10162–10167 (1988); Han et al., *Gene* (Amst.) 75: 47–57 (1989). Both the N- and C-terminal halves contain 10 cysteines and each cysteine residue's location is conserved in each half.

It has been demonstrated previously that antistasin is cleaved following Factor Xa binding. This cleavage, which occurs in the N-terminal half at arg 34, is presumed to be caused by the binding of Factor Xa (Dunwiddie et al., *J. Biol. Chem.* 264: 16694–16699 (1989)).

This invention includes the construction and production of a protein having a high degree of homology with antistasin N-terminal amino acids 1 through 58. This protein is biologically active and retains a significant portion of the Factor Xa inhibitory activity of the whole antistasin molecule.

SUMMARY OF THE INVENTION

The invention includes a protein having a molecular weight of about 6000 daltons which is biologically active in the inhibition of Factor Xa during the blood coagulation cascade, a method for producing the protein, methods for inhibiting blood coagulation using the protein, and suitable pharmaceutical compositions.

The present invention describes construction by genetic engineering and production by recombinant DNA technology of the protein of the invention. The invention also includes other versions of the protein which retain the characteristics of Factor Xa inhibitory activity and biological activity.

A preferred protein of the present invention has the following amino acid sequence

```
 1              5              10             15
Gln Gly Pro Phe Gly Pro Gly Cys Glu Glu Ala Gly Cys Pro Glu 20             25             30
Gly Ser Ala Cys Asn Ile Ile Thr Asp Arg Cys Thr Cys Ser Glu 35             40             45
Val Arg Cys Arg Val His Cys Pro His Gly Phe Gln Arg Ser Arg 50             55    58
Tyr Gly Cys Glu Phe Cys Lys Cys Arg Leu Glu Pro Met
``` or conservative amino acid substitutions thereof.

BRIEF DESCRIPTION OF THE FIGURES

FIG. 2—Construction of intermediate vector K538.
FIG. 3—Amino acid sequence of Factor Xa inhibitor with signal peptide.
FIG. 6—Antistasin variant 2 cDNA clone.

DETAILED DESCRIPTION OF THE INVENTION

Figure 1:
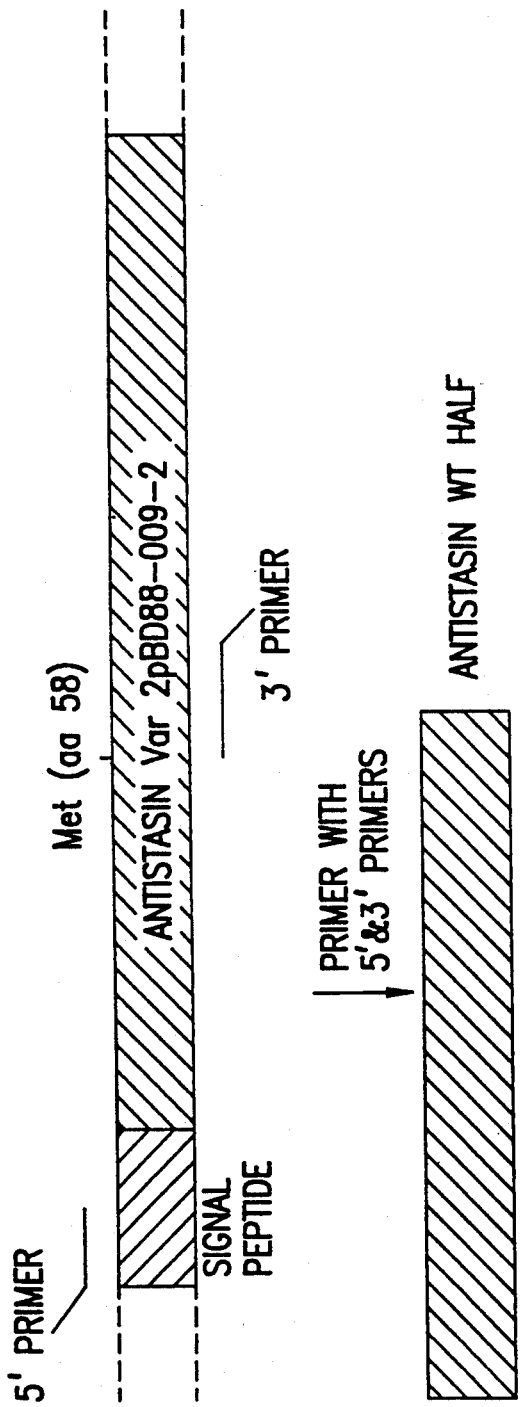
FIG. 1—Strategy and primer sequences for construction of protein cDNA molecules by PCR.

Proteins of the invention include variations on the disclosed purified protein sequence or sequences which conserve the activity of the disclosed sequence or sequences, including fragments or subunits, naturally occurring mutations, allelic variants, randomly generated artificial mutants and intentional sequence variation which conserves activity. Fragments or subunits refers to any portion of the sequence which contains fewer amino acids than the complete protein, e.g. partial sequences excluding portions at the N- and/or C-termini of the complete protein.

Proteins of the invention also include disclosed recombinant protein sequence or sequences which conserve the activity of the purified protein sequence or sequences. Also included are hybrid proteins, such as fusion proteins or proteins resulting from the expression of multiple genes within the expression vector, and may include a polypeptide having the specific activity of a disclosed protein linked by peptide bonds to a second polypeptide.

Proteins of the invention may be prepared using solid phase synthesis, such as that described by Merrifield, *J. Am. Chem. Soc.*, 85, 2149 (1964) or other equivalent chemical syntheses known in the art such as the syntheses of Houghten, *Proc. Natl. Acad. Sci.*, 82, 5132 (1985), paying particular attention to treatment of the protein-containing solution following HF cleavage. Solid-phase synthesis is commenced from the C-terminus of the peptide by coupling a protected amino acid to a suitable resin, as generally set forth in U.S. Pat. No. 4,244,946, issued Jan. 21, 1982 to Rivier et al., the disclosure of which is hereby incorporated by reference. Examples of synthesis of this general type are set forth in U.S. Pat. Nos. 4,305,872 and 4,316,891.

In synthesizing the polypeptides, the carboxyl terminal amino acid, having its alpha-amino group suitable protected, is coupled to a chloromethylated polystyrene resin or the like. After removal of the alpha-amino protecting group, as by using trifluoroacetic acid in methylene chloride, the next step in the synthesis is ready to proceed. Other standard cleaving reagents and conditions for the removal of specific amino protecting groups may be used, as described in the open literature.

The remaining alpha-amino- and side-chain-protected amino acids are then coupled stepwise in the desired order by condensation to obtain an intermediate compound connected to the resin. As an alternative to adding each amino acid separately in the synthesis, some of them may be coupled to one another prior to the addition to the growing solid-phase chain. The selection of the appropriate coupling reagents is within the skill of the art.

The condensation between two amino acids, or an amino acid and a peptide, or a peptide and a peptide can be carried out according to the usual condensation methods such as azide method, mixed acid anhydride method, DCC (dicyclohexylcarbodiimide) method, active ester method (p-nitrophenyl ester method, BOP [benzotriazole-1-yl-oxy-tris (dimethylamino) phosphonium hexafluorophosphate] method, N-hydroxysuccinic acid imido ester method, etc), Woodward reagent K method. In the case of elongating the peptide chain in the solid phase method, the peptide is attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, and t-alkyloxycarbonyl-hydrazide resin can be used.

Common to chemical syntheses of peptides is the protection of the reactive side-chain groups of the various amino acid moieties with suitable protecting groups at that site until the group is ultimately removed after the chain has been completely assembled. Also common is the protection of the alpha-amino group on an amino acid or a fragment while that entity reacts at the carboxyl group followed by the selective removal of the alpha-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The applicable protective groups for protecting the alpha- and omega-side chain amino groups are exemplified such as benzyloxycarbonyl (hereinafter abbreviated as Z), isonicotinyloxycarbonyl (iNOC), O-chlorobenzyloxycarbonyl [Z(2Cl)], p-nitrobenzyloxycarbonyl [Z(NO$_2$)], p-methoxybenzyloxycarbonyl [Z(OMe)], t-butoxycarbonyl, (Boc), t-amyloxycarbonyl (Aoc), isobornyloxycarbonyl, adamatyloxycarbonyl, 2-(4-biphenyl)-2-propyloxycarbonyl (Bpoc), 9-fluorenylmethoxycarbonyl (Fmoc), methylsulfonylethoxycarbonyl (Msc), trifluoroacetyl, phthalyl, formyl, 2-nitrophenylsulphenyl (NPS), diphenylphosphinothioyl (Ppt), dimethylphosphinothioyl (Mpt) and the like.

As protective groups for carboxy group there can be exemplified, for example, benzyl ester (OBzl), cyclohexyl ester (Chx), 4-nitrobenzyl ester (ONb), t-butyl ester (Obut), 4-pyridylmethyl ester (OPic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Mds), 1,3,5-trimethylphenysulfonyl (Mts), and the like. The thiol group in cysteine may be protected with p-methoxybenzyl, triphenylmethyl, acetylaminomethyl, ethylcarbamoyle, 4-methylbenzyl, 2,4,6-trimethybenzyl (Tmb) etc, and the hydroxyl group in serine can be protected with benzyl, t-butyl, acetyl, tetrahydropyranyl etc.

Stewart and Young, "Solid Phase Peptide Synthesis", Pierce Chemical Company, Rockford, Ill. (1984) provides detailed information regarding procedures for preparing peptides. Protection of α-amino groups is described on pages 14–18, and side-chain blockage is described on pages 18–28. A table of protecting groups for amine, hydroxyl and sulfhydryl functions is provided on pages 149–151. These descriptions are hereby incorporated by reference.

After the desired amino-acid sequence has been completed, the intermediate peptide is removed from the resin support by treatment with a reagent, such as liquid HF and one or more thio-containing scavengers, which not only cleaves the peptide from the resin, but also cleaves all the remaining side-chain protecting groups. Following HF cleavage, the protein sequence is washed with ether, transferred to a large volume of dilute acetic acid, and stirred at pH adjusted to about 8.0 with ammonium hydroxide.

Preferably in order to avoid alkylation of residues in the polypeptide, (for example, alkylation of methionine, cysteine, and tyrosine residues) a thio-cresol and cresol scavenger mixture is used. The resin is washed with ether, and immediately transferred to a large volume of dilute acetic acid to solubilize and minimize intermolecular cross-linking. A 250 μM polypeptide concentration is diluted in about 2 liters of 0.1M acetic acid solution. The solution is then stirred and its pH adjusted to about 8.0 using ammonium hydroxide. Upon pH adjustment, the polypeptide takes its desired conformational arrangement.

Recombinant DNA Technology

Recombinant DNA technology may be used to produce proteins of the invention. This technology allows segments of genetic information, DNA, from different cells, and usually from different organisms, to be joined end-to-end outside the organisms from which the DNA was obtained and to incorporate this hybrid DNA into a cell that will allow the production of the protein for which the original DNA encodes. Genetic information, DNA or mRNA, is isolated and incorporated into an appropriate cloning vector, and transduced into an appropriate host cell.

Cloning vectors useful for this technology include a DNA sequence which accommodates specific experimental foreign DNA. The vectors are introduced into host cells that can exist in a stable manner and express the protein dictated by the experimental DNA. Cloning vectors may include plasmids, bacteriophage, viruses and cosmids.

Expression vectors are DNA sequences that are required for the transcription of cloned copies of genes and the translation of their mRNAs in an appropriate host. These vectors can express either procaryotic or eucaryotic genes in a variety of cells such as bacterial, yeast, insect and mammalian cells.

Proteins may also be expressed in a number of virus systems. A suitably constructed expression vector contains an origin of replication for autonomous replication in host cells, selective markers, a limited number of useful restriction enzyme sites, a high copy number, and strong promoters. Promoters are DNA sequences that direct RNA polymerase to bind to DNA and initiate RNA synthesis; strong promoters cause such initiation at high frequency. Expression vectors may include, but are not limited to cloning vectors, modified cloning vectors and specifically designed plasmids or viruses.

Expression Systems

Procaryotes most frequently are represented by various strains of E. coli. Other microbial strains may be used, such as bacilli, e.g. *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., *Gene* (1977) 2:95. Commonly used procaryotic control sequences, which are defined herein to include promoters for transcription initiation, optionally with an operator, along with ribosome binding site sequences, include such commonly used promoters as the beta-lactamase (penicillinase) and lactose (lac) promoter systems (Chang et al., *Nature* (1977) 198:1056) and the tryptophan (Trp) promoter system (Goeddel et al., *Nucleic Acids Res.* (1980) 8:4057) and the lambda-derived $P_L$ promoter and N-gene ribosome binding site (Shimatake et al., *Nature* (1981) 292:128). However, any available promoter system compatible with procaryotes can be used.

Expression systems useful in the eucaryotic systems of the invention comprise promoters derived from appropriate eucaryotic genes. A class of promoters useful in yeast, for example,, include promoters for synthesis of glycolytic enzymes, including those for 3-phosphoglycerate kinase (Hitzeman et al., *J. Biol. Chem.* (1980) 255:2073). Other promoters include those from the enolase gene (Holland, M. J., et al., *J. Biol. Chem.* (1981) 256:1385) or the Leu2 gene obtained from YEp13 (Broach, J., et al., *Gene* (1978) 8:121).

Suitable mammalian promoters including the early and late promoters from SV40 (Fiers, et al., *Nature* (1978) 273:113) or other viral promoters such as those derived from polyoma, adenovirus II, bovine papilloma virus or avian sarcoma viruses. Suitable viral and mammalian enhancers are cited above. In the event plant cells are used as an expression system, the nopaline synthesis promoter is appropriate (Depicker, A. et al., *J. Mol. Appl. Gen.* (1982) 1:561).

Insect cell expression systems useful for expressing the proteins include the modified versions of the system described in Smith et al., U.S. Pat. No. 4,745,051. Baculovirus DNA comprising a baculovirus gene or a portion thereof which includes a promoter of the baculovirus gene is cleaved to obtain a DNA fragment containing at least the promoter. The desired product protein is prepared by infecting a susceptible host insect cell with a recombinant baculovirus expression vector wherein the expression vector is a recombinant baculovirus genome comprising at least one selected heterologous product protein polypeptide structural gene under the transcriptional control of a baculovirus polyhedrin promoter.

A recombinant baculovirus expression vector capable of expressing a selected gene in a host insect cell is produced by cleaving baculovirus DNA to produce a DNA fragment comprising a baculovirus polyhedrin promoter, and sufficient flanking DNA sequences to facilitate homologous recombination; inserting the baculovirus DNA fragment into a cloning vehicle to form a modified cloning vector; identifying a selected restriction site of the cloned baculovirus DNA fragment which is under the transcriptional control of the baculovirus polyhedrin promoter; deleting from the modified cloning vector the additional restriction site in the baculovirus DNA fragment under the transcriptional control of the baculovirus polyhedrin promoter; inserting a selected heterologous gene into the unique restriction site to form a recombinant shuttle vector; contacting the baculovirus DNA so as to effect recombination, thereby producing a mixture of recombinant and nonrecombinant baculoviruses; and isolating a recombinant baculovirus expression vector from the mixture.

Oligonucleotide Primers

Oligonucleotide primers are prepared which will hybridize to different strands of the desired sequence and at relative positions along the sequence such that an extension product synthesized from one primer, when it is separated from its template (complement), can serve as a template for extension of the other primer into a nucleic acid of defined length. The primers may be prepared using any suitable method, such as, for example, the phosphotriester and phosphodiester methods, described respectively in Narang, S.A., et al. *Meth. Enzymol.*, 68, 90 (1979) and Brown, E.L. et al., *Meth. Enzymol*, 68, 109 (1979), or automated embodiments thereof. In one such automated embodiment, diethylphosphoramidites are used as starting materials and may be synthesized as described by Beaucage et al., *Tetrahedron Letters* (1981), 22: 1859-1862. One method for synthesizing oligonucleotides on a modified solid support is described in U.S. Pat. No. 4,458,066. It is also possible to use a primer which has been isolated from a biological source (such as a restriction endonuclease digest).

Probing cDNA Libraries cDNA or genomic libraries are screened using the colony or plaque hybridization procedure. Each plate containing bacterial colonies (or recombinant phage-infected bacteria) is replicated onto duplicate nitrocellulose filter papers (S & S type BA-85) and, for bacterial colony screens, the colonies are allowed to grow at 37° C. for 14–16 hours on L agar containing 50 μg/ml Amp. The bacteria are lysed plasmid or phage and DNA fixed to the filter by sequential treatment for 5 minutes each time with 0.2N NaOH, 1.5M NaCl, then 0.5M Tris pH 7.5, 1.5M NaCl and then 2×standard saline citrate (2×SSC). Filters are air dried and baked at 80° C. for 2 hours. The duplicate filters are prehybridized at 42° C. for 6-8 hours with 10 ml per filter of DNA hybridization buffer (5×SSC, pH 7.0, 5×Denhardt's solution (polyvinyl pyrrolidine, plus Ficoll and bovine serum albumin; 1×=0.02% of each), 50 mM sodium phosphate buffer at pH 7.0, 0.2% SDS, 20 μg/ml polyU, and 50 μg/ml denatured salmon sperm DNA.

The samples are hybridized with kinased probe under conditions which depend on the stringency desired. Typical moderately stringent conditions employ a temperature of 42° C. for 24-36 hours with 1-5 ml/filter of DNA hybridization buffer containing probe. For higher stringencies, high temperatures and shorter times are employed. The filters are washed four times for 30 minutes each time at 37° C. with 2×SSC, 0.2% SDS and 50 mM sodium phosphate buffer at pH 7, then are washed twice with 2×SSC and 0.2% SDS, air dried and are autoradiographed at −70° C. for 2 to 3 days.

Polymerase Chain Reaction Amplification

Large amounts of DNA coding for the protein may be obtained using polymerase chain reaction (PCR) amplification techniques as described in Mullis et al., U.S. Pat. No. 4,800,159. The extension product of one primer, when hybridized to another primer, becomes a template for the production of the nucleic acid sequence.

The primer template complexes act as substrate for DNA polymerase which, in performing its replication function, extends the primers. The region in common with both primer extensions, upon denaturation, serves as template for a repeated primer extension.

Taq DNA Polymerase catalyzes primer extension in the amplification process. The enzyme is a thermostable DNA polymerase isolated from *Thermus aquaticus*. Because it stays active through repeated elevations to high denaturation temperatures, it needs to be added only once. Deoxynucleotide triphosphates provide the building blocks for primer extension.

The nucleic acid sequence strands are heated until they separate, in the presence of oligonucleotide primers that bind to their complementary strand at a particular site of the template. This process is continued with a series of heating and cooling cycles, heating to separate strands, and cooling to reanneal and extend the sequences. More and more copies of the strands are generated as the cycle is repeated. Through amplification, the coding domain and any additional primer-encoded information such as restriction sites or translation signals (signal sequences, start codons and/or stop codons) is obtained. PCR protocols are often performed at the 100 $\mu$L scale in 0.5-mL microcentrifuge tubes. The PCR sample may be single-or double-stranded DNA or RNA. If the starting material is RNA, reverse transcriptase is used to prepare first strand cDNA prior to PCR. Typically, nanogram amounts of cloned template, up to microgram amounts of genomic DNA, or 20,000 target copies are chosen to start optimization trials.

PCR primers are oligonucleotides, typically 15 to 30 bases long, and are complementary to sequences defining the 5' ends of the complementary template strands. Non-template complementary 5' extensions may be added to primers to allow a variety of useful post amplification operations on the PCR product without significant perturbation of the amplification itself. It is important that the two PCR primers not contain more than two bases complementary with each other, especially at their 3' ends. Internal secondary structure should be avoided in primers.

Because Taq DNA Polymerase has activity in the 37°–55° C. range, primer extension will occur during the annealing step and the hybrid will be stabilized. The concentrations of the primers preferably equal in conventional PCR and, typically, within 0.1-to 1-$\mu$M range.

In the standard PCR protocol, each deoxynucleotide triphosphate concentration is preferably about 200 $\mu$M. The four dNTP concentrations are preferably above the estimated Km of each dNTP (10–15 $\mu$M).

Preferably PCR buffer is composed of about 500 mM potassium chloride, 100 mM Tris-HCl (pH 8.3 at room temperature), 15 mM magnesium chloride, and 0.01% w/v gelatin. In the presence of 0.8 mM total dNTP concentration, a titration series in small increments over the 1.5-to 4-mM range will locate the magnesium concentration producing the highest yield of a specific product. Too little free magnesium will result in no PCR product and too much free magnesium may produce a variety of unwanted products.

Preferably, in a 100-$\mu$L reaction volume, 2.0 to 2.5 units of Taq DNA Polymerase are recommended. The enzyme can be added conveniently to a fresh master mix prepared for a number of reactions, thereby avoiding accuracy problems associated with adding individual 0.5-$\mu$L enzyme aliquots to each tube. A typical PCR protocol for amplification of the DNA template includes a 1 minute 94° C. denaturation step, a 1 minute 37° C. primer annealing step, and a 2 minute 72° C. primer extension step. This will amplify a 500 base-pair product at least 100,000-fold in 25 cycles.

During DNA denaturation, sufficient time must be allowed for thermal equilibration of the sample. The practical range of effective denaturation temperatures for most samples is 92°–95° C., with 94° C. being the standard choice.

Primer annealing is usually performed first at 37° C., and the specificity of the product is evaluated. If unwanted bands are observed, the annealing temperature should be raised in subsequent optimization runs. While the primer annealing temperature range is often 37°–55° C., it may be raised as high as the extension temperature in some cases. Merging of the primer annealing and primer extension steps results in a two-step PCR process.

Primer extension, in most applications, occurs effectively at a temperature of 72° C. and seldom needs optimization. In the two-temperature PCR process the temperature range may be 65°–70° C. In situations where enzyme concentration limits amplification in late cycles, the extension is preferably increased linearly with cyclic number. Usually, 25 to 45 cycles are required for extensive amplification (i.e., 1,000,000 fold) of a specific target.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g. New England Biolabs, Product Catalog. In general, about 1 microgram of plasmid or DNA sequence is cleaved by one unit of enzyme in about 20 $\mu$l of buffer solution (at 37° C.). Typically, an excess of restriction enzyme is used to ensure complete digestion of the DNA substrate. Incubation times of about 1 to 2 hours at about 37° C. are workable, although variations can be tolerated. After each incubation, protein is removed by extraction with phenol/chloroform, and may be followed by running over a Sephadex ® G-50 spin column. If desired, size separation of the cleaved fragments may be performed by polyacrylamide gel or agarose gel electrophoresis using standard techniques. A general description of size separations is formed in *Methods in Enzymology* (1980)65: 499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20 to 25° C. in 50 mM Tris, pH 7.6, 50 mM NaCl, 6 mM MgCl$_2$, 6 mM DTT and 5-10 μMdNTPs. The Klenow fragment fills in 5' overhangs but removes protruding 3' single strands, even in the presence of the four dNTPs. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex® G-50 spin column. Treatment under appropriate conditions with S1 nuclease results in hydrolysis of any single-stranded portion.

As mentioned above, oligonucleotides may be prepared by the triester method of Matteucci, et al. (*J. Am. Chem. Soc.* (1981) 103:3185) or using commercially available automated oligonucleotide synthesizers. Kinasing of single strands prior to annealing or for labelling is achieved using an excess, e.g., approximately 10 units of polynucleotide kinase to 0.1 nmole substrate in the presence of 50 mM Tris, pH 7.6, 10 mM MgCl$_2$, 5 mM dithiothreitol, 1-2 mM ATP, 1.7 pmoles $^{32}$P-ATP(2.9 mCi/mmole), 0.1 mM spermidine, 0.1 mM EDTA.

Ligations are performed in 15-30 μl volumes under the following standard conditions and temperatures: 20 mM Tris-HCl, pH 7.5, 10 mM MgCl$_2$, 10 mM DTT, 33 μg/ml BSA, 10 mM-50 mM NaCl, and 1 mM ATP, 0.3-0.6 (Weiss) units T4 DNA ligase at 14° C. (for "blunt end" ligation). Intermolecular "sticky end" ligations are usually performed at 33-100 μg/ml total DNA concentrations (5-100 nM total end concentration). Intermolecular blunt end ligations (usually employing a 10-30 fold molar excess of linkers) are performed at 1 μM total ends concentration.

In vector construction employing "vector fragments," the vector fragment is commonly treated with bacterial alkaline phosphatase (BAP) or calf intestine alkaline phosphatase (CIAP), reaction at 37° C., 30 minutes, in order to remove the 5' phosphate and prevent religation of the vector. BAP digestions are conducted at pH 8 in approximately 150 mM Tris, in the presence of Na$^+$ and Mg$^{2+}$ using about 1 unit of BAP per μg of vector at 60° C. for about 1 hour. In order to recover the nucleic acid fragments, the preparation is extracted with phenol/chloroform and ethanol precipitated and desalted by application to a Sephadex® G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used. This is conducted using a primer synthetic oligonucleotide complementary to a single stranded plasmid or phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

Verification of Construction

In the constructions set forth below, correct ligations for plasmid construction are confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc. Natl. Acad. Sci. USA* (1969) 62:1159, optionally following chloramphenicol amplification (Clewell, D. B., *J. Bacteriol* (1972) 110:667). The isolated DNA is analyzed by restriction and/or sequenced by the dideoxy method of Sanger, F., et al, *Proc. Natl. Acad. Sci. USA* (1977) 74:5463 as further described by Messing, et al, *Nucleic Acids Res* (1981) 9:309, or by the method of Maxam, et al, *Methods in Enzymology* (1980) 65:499.

Transformation

Depending on the host cell used, transformation is done using standard techniques appropriate to such cells. The calcium treatment employing calcium chloride, as described by Cohen, S. N., *Proc. Natl. Acad. Sci. USA* (1972) 69:2110, or the RbCl method described in Maniatis et al., *Molecular Cloning: A Laboratory Manual* (1982) Cold Spring Harbor Press, p. 254 is used for procaryotes or other cells which contain substantial cell wall barriers. Infection with *Agrobacterium tumefaciens* (Shaw, C. H., et al., *Gene* (1983) 23:315) is used for certain plant cells. For mammalian cells without such cell walls, the calcium phosphate precipitation method of Graham and van der Eb, *Virology* (1978) 52:546 is preferred. Transformations into yeast are carried out according to the method of Van Solingen, P., et al., *J. Bacter.* (1977) 130:946 and Hsiao, C. L. et al., *Proc. Natl. Acad. Sci. USA* (1979) 76:3829.

EXAMPLE 1

Production of Factor Xa Inhibitor in Spodoptera frugiperda Sf9 Insect Cells

The antistasin variant 2 cDNA clone (FIG. 6) from lambda gt22 cDNA expression library (Han et al., *Gene* 75: 47-57 (1989)), which is flanked by NotI and SalI, was digested with Not I/Sal I. Restriction enzyme sites were subcloned into pUC18 intermediate vector (Bethesda Research Laboratories) at NotI/SalI restriction enzyme sites, to yield the intermediate vector K538 (FIG. 2).

K538 was digested with AvaII and HindIII (FIG. 2), and missing sequences at both ends of antistasin ORF were refilled by ligation with the following oligonucleotide sequences:

1. 5'-AATTCGCGGCCGCCATACGATTTAGGTGACACTA-
   TAGAATTTTTTTTTTTTTTT-3'

2. 5'-AATTCGTCGACAATACGACTCACTATAGGGAGAC-
   CCCCCCCCCCCCCC-3'

3. 
```
           C          C
   5'-GGCATGATGTG AGCCGC TGACTAATAAGTG-
                 T      T
      C      C
      GATTG AAGATTGATATTAATGCCGCAAG-3'
      T     T
```

4. 
```
           G           G          G
   5'-TTC CAGTATTC CAGCCCA CTTATCGCGCTT-
          A        A       A
      G        G
      CA GCCATTCGG CAAGTCTTGCGGCAATTAATATC-3'
      A         A
```

Figure 4:
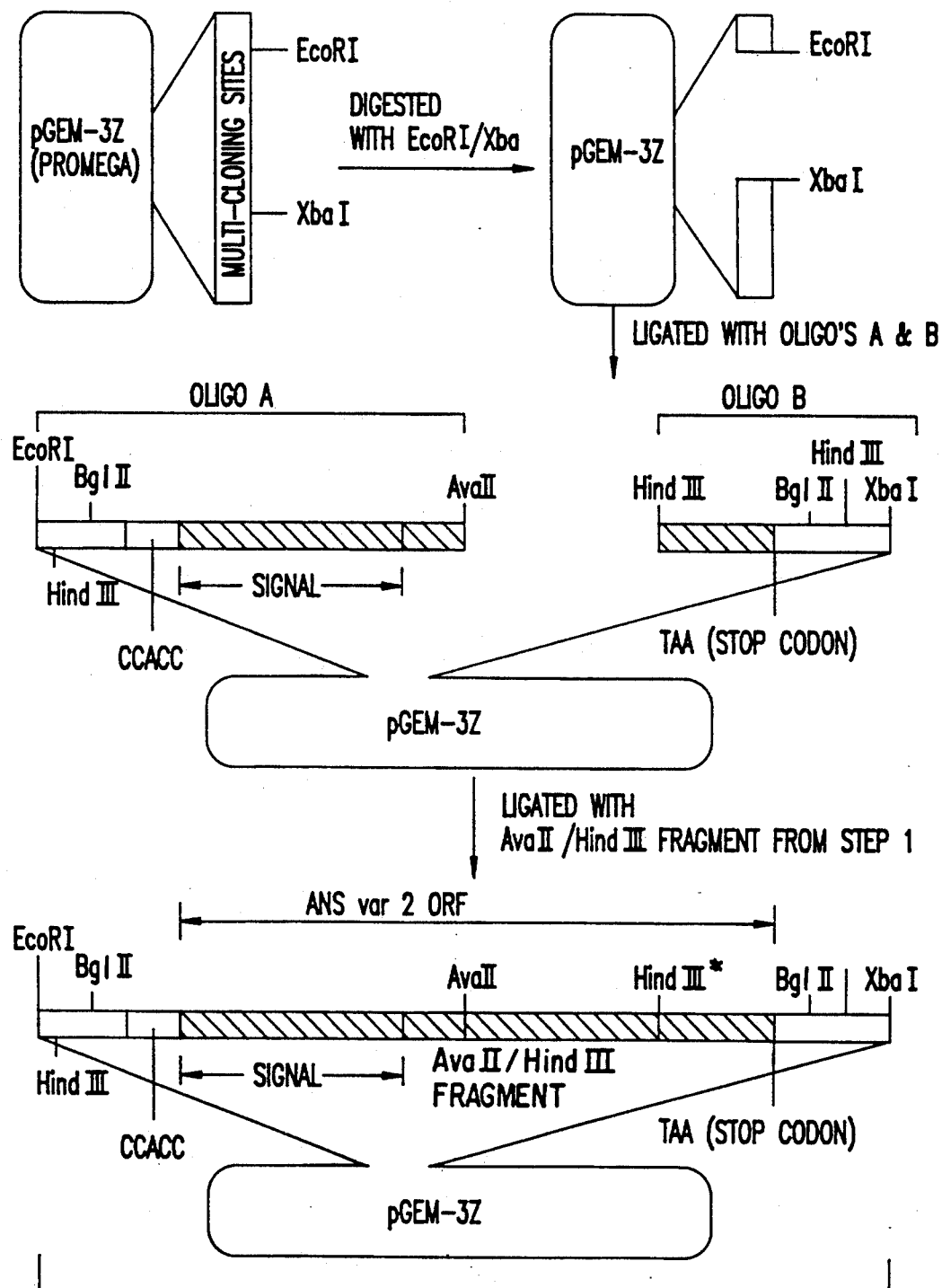
FIG. 4—Construction of intermediate vector pBD88-009-2.

PBD88-009-2 was constructed as follows (FIG. 4). pGEM-3Z (Promega Biotec) was digested with EcoRI/XbaI. Digested pGEM-3Z was ligated first with oligo A and oligo B, digested with Ava II, HindIII and then ligated to with the AvaII/HindIII fragment previously obtained from digested K538. The resultant pBD88-009-2 thus contains the complete antistasin variant 2 ORF. pBD88-009-2 was used as a template for PCR amplification with a 5' primer containing Bam HI cloning site, Kozak sequence (CCACC) ascertaining a proper initiation (Kozak, *Nucleic Acids Res.* 15: 8125-8148 (1987)), followed by an initiation codon (ATG) and sequences of amino acid residues 2-5; and a 3' primer containing sequences of amino acid residues 55-58 followed by a stop codon (TTA) to terminate translation and a Bam HI cloning site (GGATCC) for subcloning (FIG. 1).

Figure 5:
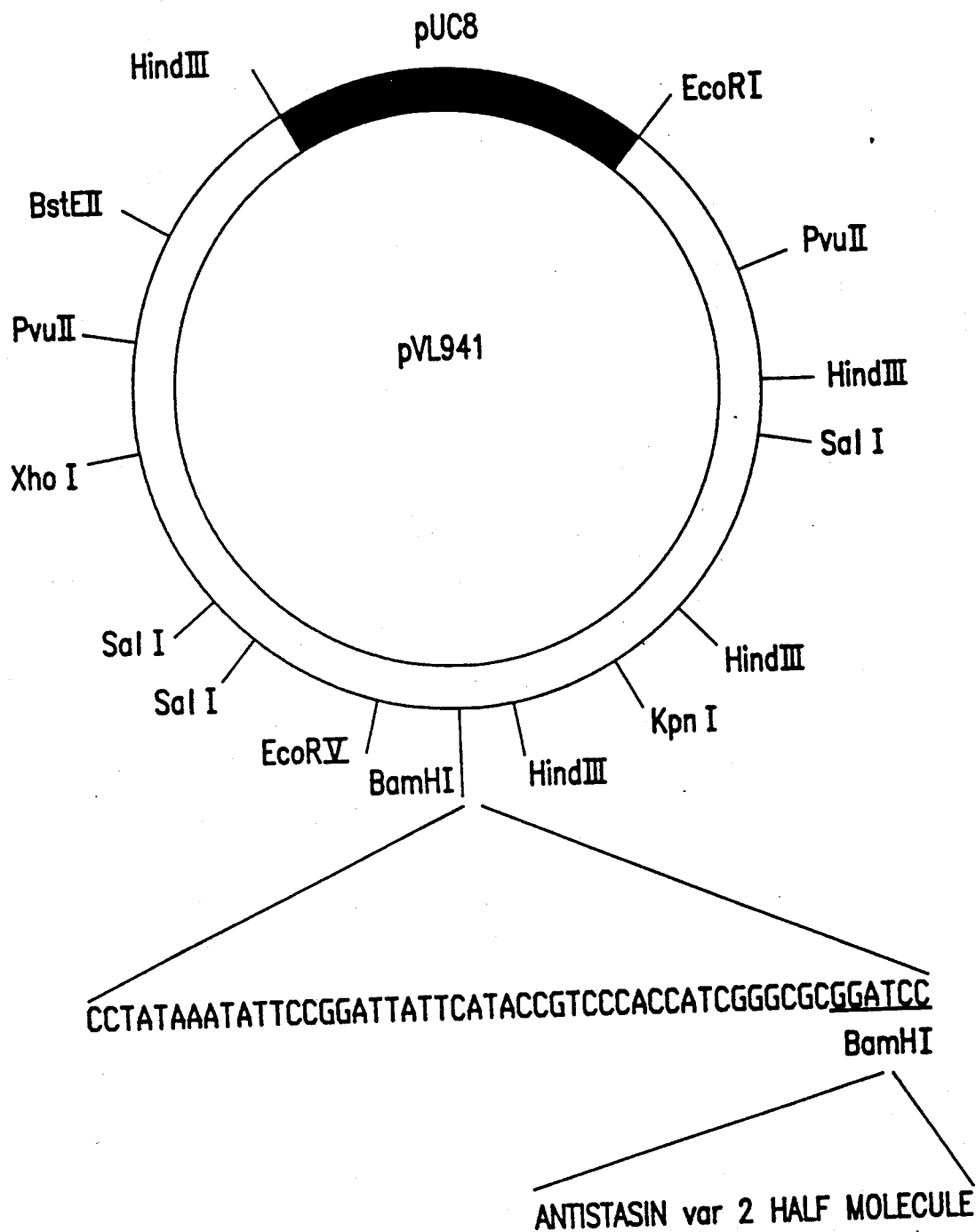
FIG. 5—Expression vector pWO88-12.

PCR amplification was carried out with a DNA thermal cycler (Perkin Elmer Cetus) according to Saiki et al., *Science* 239: 487-491 (1988), in 100 ul volume containing 50 mM KCl, 10 mM Tris, pH 8.3, 1.5 mM MgCl$_2$, 0.01% gelatin, 200 um of each of deoxynucleotide triphosphate (dNTP) and 2.5 units of Taq polymerase (Perkin Elmer Cetus) with 10 ng of the DNA template pBD88-009-2 containing var 2 Antistasin and 500 ng (0.1 nmoles) of each of the primers. The reaction mixture was overlaid with 100 ul light mineral oil (Sigma) to prevent evaporation. The following PCR amplification program was used: initial template denaturation step: 8 minutes at 94° C., afterwards: 2 minutes at 94° C., 3 minutes at 60° C., 3 minutes at 72° C., for 30 cycles. The completed PCR reactions were extracted once with chloroform to remove the mineral oil and 5 ul was resolved on a 2% agarose gel and DNAs were visualized with a UV light following ethidium bromide staining. Residual PCR primers and dNTPs were removed by dilution with water and passage through a Centricon 30 membrane (Amicon). The PCR products were then digested with the restriction enzyme Bam HI (Boehringer Mannheim) to generate cloning sites and gel purified using NA-45 ion exchange membrane (Schleicher & Scheull). Eluted DNA was phenol/chloroform extracted, ethanol precipitated, centrifuged, redissolved in water and ligated into the Bam HI sites of the intermediate expression vector pSP73 (Promega) with T4 DNA ligase (Boehringer Mannheim) to form pJD88-08. The 58 amino acid cDNA was digested from pJD88-08 with BamHI and ligated into an *Autographa californica* nuclear polyhedrosis virus (AcNPV) expression vector, pVL941 (Luckow and Summers, *Virology* 170: 31-39 (1989)), to form pWO88-12 (FIG. 5). pWO88-12 includes the amino acid sequence of the 58 amino acid molecule with signal peptide (FIG. 3 shows this sequence with the signal peptide underlined and the amino acid residue at the N-terminus of the mature protein numbered as +1.)

*E. coli* HB101 competent cells (Bethesda Research Laboratories) were transformed with the recombinant intermediate expression vector pJD88-08 by a modified method of Hanahan (*J. Mol. Biol.* 166: 557 (1983)) and a large scale preparation of plasmid DNA was performed as described in Maniatis, *A. Cloning Manual* (alkaline lysis method). In vitro transcription and translation was carried out using this construct as described by the Riboprobe system (Promega). In vitro translation products were resolved by SDS-PAGE as described above and an autoradiograph showed that a protein product of the predicted size was produced by the recombinant intermediate vectors, indicating that the inserted cDNA reading frame of the genetically engineered et al., In Vitro (1977) 13, 231+) derived from pupal ovary tissue of Fall Army Worm *Spodopetra frugiperda* ATCC No. CRL 1711) was used as a host cell antistasin half molecule is functional, i.e., there are no detrimental point mutations, deletions or insertions.

Expression in insect cells

*Spodoptera frugiperda* Sf9 insect cells (a clonal isolate of the cell line IPLB-Sf21-AE (Vaughan et al., In Vitro (1977) 13, 231+) derived from pupal ovary tissue of Fall Army Worm *Spodopetra frugiperda* ATCC No. CRL 1711) was used as a host cell.

pWO88-12 was used to cotransfect the cells by the method of Summers and Smith (Texas Agricultural Experimental Section Bulletin No. 1555, 1987). pWO88-12 contains the 58 amino acid protein gene inserted down-stream of the polyhedrin promoter. After 5 days, virus were recovered and plaque purified according to Summers and Smith. Viral plaques exhibiting the morphological characteristic of recombinant virus infection were picked as a source of viral stocks. The extracellular virus (ECV) of these isolates were used to infect Sf9 cells and in 5 days generated culture medium suitable for assay for secreted protein.

IPL-41 basal medium (from J. R. Scientific, Woodland, Calif.) with 2% heat-inactivated Fetal Bovine Serum (FBS, Gibco, Grand Island, N.Y.) 3.3 g/l yeastolate (Difco, Detroit, Mich.) was used for both static and suspension cultures, except that 1.0 g/l Pluronic F68 (BASF Corporation, Parsippany, N.J.) was added to suspension cultures. Cells were grown to a dessity of $1.0 \times 10^6$ cells/ml in spinner flasks, and virus was added at a concentration of 10 ml virus stock having viral titer of $10^7$ plaque forming units per ml added per liter of culture. Sf9 cell growth and viral infection were found to be adversely affected by too low (below 20% air saturation) or too high (over 100%) a level of dissolved oxygen in the culture medium. Culture medium containing the virus was harvested between 72 and 96 hours.

Verification of protein expression

The presence of active proteins in culture media was identified by Factor Xa inhibition assays using the chromagenic substrate assay system Spectrozyme Factor Xa (American Diagnostica). To 100 ul of 50 mM Tris, pH 7.5, 0.15M NaCl, 0.1% BSA (TBSA buffer) was added 10 ul culture medium (or TBSA buffer for controls) and 50 ul of Factor Xa (0.5 nM final concentration) and the mixture was incubated at 20°-23° C. for 30 minutes. Sixty ul of Spectrozyme Factor Xa was added to all samples and enzyme activity was determined by measuring the increase of absorbance at 405 nm using a BioRad model 3550 microplate reader. Culture media collected 4 days post infection were shown to contain Factor Xa inhibitory activity. These culture media were then concentrated by Centricon membrane 10 and analyzed by immunoblot. Concentrated culture media were denatured with 0.3% SDS and reduced with 2% (v/v) 2-mercaptoethanol, resolved by electrophoresis on a 12% polyacrylamide gel, Lammeli, Nature 227: 680-685 (1970), electro-transferred onto a Gene Screen plus nylon membrane (NEN/DuPont) according to the manufacturer's instructions, probed with a guinea pig anti-antistasin antiserum followed by $^{125}$I-protein A (NEN/DuPont). An autoradiograph of the immunoblot showed a protein band with the predicted molecular size of 6 kDa for antistasin half molecules in the culture media shown to contain Factor Xa inhibitory activities but not from the uninfected control cell cultures.

For the purpose of further biochemical characterization, recombinant proteins were partially purified from the culture media by heparin-Sepharose chromatography. The culture medium was diluted 1 to 6 with loading buffer (20 mM Tris, pH 5.6 containing 0.01% Tween 80) before loading, washed with loading buffer and eluted stepwise with 0.15-0.75M NaCl. (0.15, 0.25, 0.35, 0.45, 0.55, 0.65, 0.75) Active proteins were eluted by 0.15M NaCl. Eluates were then desalted, concentrated and exchanged into 20 mM Tris buffer, pH 7.4 using a Centricon 10 membrane. For the purpose of producing larger amounts of protein for in vivo efficacy and safety evaluations, a batch method using reverse phase HPLC matrix was employed. Cell-free culture medium from baculovirus/Sf9 cells was filtered through a 0.22 micron cellulose acetate membrane. Bulk prep $C_{18}$ reverse phase packing resin (Waters) was adjusted to with 5% isopropanol (IPA) and mixed with filtered medium, which had been pre-adjusted to 5% IPA. Most of the Factor Xa inhibitory activity was found to be efficiently eluted from the resin with 20% IPA. The recovery of Factor Xa inhibitory activity at this stage was 50% of that found in the starting medium. This eluate was further purified by preparative isoelectric focusing followed by elution from a RP-HPLC using u-Bonkapak $C_{18}$ column with a 5-30% linear gradient of acetonitrile in 0.1% TFA. Two Factor Xa inhibitory peaks were recovered with the later eluted one containing 80% of the activity. The total recovery of Factor Xa inhibitory activity at this stage was 47%.

The two Factor Xa inhibitory peaks were shown to be equally active in Factor Xa inhibition, with similar $IC_{50}$ (0.73 nM) as determined as above, and were similar in amino acid compositions (Table 1) which was determined as follows. Protein hydrolysis was done under vacuum in 6N HCl, 0.1% phenol at 110° C. for 70 hours. Amino acid analysis was carried out using a Beckman Model 6300 amino acid analyzer with ninhydrin post-column detection as specified by the manufacturer. The different elution pattern of these two peaks may be due to post-translational modification or aggregation.

TABLE 1

| Residue | Theoretical | | Experimental | |
| --- | --- | --- | --- | --- |
| | Var 2 | (Var 1) | Major peak | Minor peak |
| Asx | 2 | | 2.3* 1.93* | 2.27 |
| Thr | 2 | | 1.8 1.94 | 1.96 |
| Ser | 3 | | 2.7 2.78 | 2.68 |
| Glx | 8 | (7) | 7.6 8.05 | 7.39 |
| Pro | 5 | | 5.1 4.60 | 4.62 |
| Gly | 7 | (8) | 6.5 6.89 | 6.25 |
| Ala | 2 | | 1.9 2.23 | 2.14 |
| Cys | 10 | | N.D. N.D. | N.D. |
| Val | 2 | (1) | 1.9 2.49 | 2.27 |
| Met | 1 | (2) | N.D. 0.81 | 0.75 |
| Ile | 2 | (3) | 1.9 1.15 | 1.19 |
| Leu | 1 | | 1.4 1.21 | 1.35 |
| Tyr | 1 | | 1.0 1.03 | 0.97 |
| Phe | 3 | | 2.9 2.99 | 2.78 |
| His | 2 | | 2.0 1.77 | 1.74 |
| Lys | 1 | | 1.2 1.13 | 1.52 |
| Arg | 6 | (5) | 5.0 4.88 | 4.47 |

*Two separate determinations

The protein of the invention inhibits coagulation pathway by inhibiting Factor Xa. Factor Xa inhibition is achieved by administering the protein, either by continuous intravenous administration or bolus administration, in combination with a suitable pharmaceutical composition carrier e.g., saline, at a suitable pH, e.g., 7.4, such that the composition achieves the desired effect of preventing Factor Xa from inducing formation of thrombin from prothrombin.

The proteinaceous substance of this invention having Factor Xa inhibition activity can, like many proteins/peptides, form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, trifluoroacetic, glutaric, fumaric, malic, tartaric, citric, ascorbic, maleic, hydroxymaleic, benzoic, hydroxybenzoic, phenylacetic, cinnamic, salicyclic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminium; and organic primary, secondary and tertiary amines, as for example, trialkylamines, including triethylamine, procaine, dibenzylamine, 1-ethenamine; N,N'-dibenzylethylenediamine, dihydroabietylamine, N-(lower)alkylalkylpiperidine, and any other suitable amine.

The anticoagulant dose of the proteinaceous substance of this invention having Factor Xa inhibition activity is from 0.4 mg/kg to 500 mg/kg of patient body weight per day depending on, for example, the patient, and the severity of the thrombotic condition to be treated. The suitable dose for a particular patient can be readily determined. Preferably from 1 to 4 daily doses would be administered typically with from 10 mg to 200 mg of active compound per dose. The concentration of the proteinaceous substance of this invention having Factor Xa inhibition activity required to inhibit Factor Xa when used to inhibit blood coagulation or Factor Xa in a medium such as stored blood can be readily determined by those skilled in the art.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice. Inhibition of Factor Xa is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the proteinaceous substance of this invention having Factor Xa inhibition activity can be added to or contacted with any medium containing or suspected of containing Factor Xa and in which it is desired that blood coagulation be inhibited.

Although the proteinaceous substance of this invention having Factor Xa inhibition activity may survive passage through the gut following oral administration, applicants prefer non-oral administration, for example, subcutaneous, intravenous, intramuscular or intraperitoneal; administration by depot injection; or by implant preparation.

for parenteral administration the proteinaceous substance of this invention having Factor Xa inhibition activity may be administered as injectable dosages of a solution or suspension of the substance in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The proteinaceous substance of this invention having Factor Xa inhibition activity can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The protein may be used alone or in combination with other proteins. For example, the protein enhances the efficiency of tissue plasminogen activator-mediated thrombolytic reperfusion. It may be administered first following thrombus formation, and tissue plasminogen activator or other plasminogen activator is administered thereafter.

What is claimed is:

1. A protein having a approximate molecular weight of 6000 daltons and having the following sequence:

```
1               5              10              15
Gln Gly Pro Phe Gly Pro Gly Cys Glu Glu Ala Gly Cys Pro Glu 20              25              30
Gly Ser Ala Cys Asn Ile Ile Thr Asp Arg Cys Thr Cys Ser Glu 35              40              45
Val Arg Cys Arg Val His Cys Pro His Gly Phe Gln Arg Ser Arg 50              55      58
Tyr Gly Cys Glu Phe Cys Lys Cys Arg Leu Glu Pro Met
```

2. A therapeutic composition for inhibiting blood coagulation comprising an effective amount of the protein of claim 1 and a pharmaceutically acceptable carrier.

3. A method for inhibiting blood coagulation in a mammal comprising administering to the mammal an effective dose of a composition of claim 2.

* * * * *